US009632028B2

(12) United States Patent
Goshoo et al.

(10) Patent No.: US 9,632,028 B2
(45) Date of Patent: Apr. 25, 2017

(54) DRYNESS MEASUREMENT DEVICE

(71) Applicant: Azbil Corporation, Tokyo (JP)

(72) Inventors: Yasuhiro Goshoo, Tokyo (JP); Giichi Nishino, Tokyo (JP); Shiko Tanabe, Tokyo (JP)

(73) Assignee: Azbil Corporation, Tokyo (JP)

( * ) Notice: Subject to any disclaimer, the term of this patent is extended or adjusted under 35 U.S.C. 154(b) by 0 days.

(21) Appl. No.: 15/108,509

(22) PCT Filed: Oct. 29, 2014

(86) PCT No.: PCT/JP2014/078830
§ 371 (c)(1),
(2) Date: Jun. 27, 2016

(87) PCT Pub. No.: WO2015/098279
PCT Pub. Date: Jul. 2, 2015

(65) Prior Publication Data
US 2016/0327482 A1 Nov. 10, 2016

(30) Foreign Application Priority Data
Dec. 27, 2013 (JP) .................................. 2013-272668

(51) Int. Cl.
G01N 21/00 (2006.01)
G01N 21/59 (2006.01)
(Continued)

(52) U.S. Cl.
CPC .............. *G01N 21/59* (2013.01); *F01K 5/00* (2013.01); *F01K 5/02* (2013.01); *F01K 13/003* (2013.01);
(Continued)

(58) Field of Classification Search
CPC ............. G01N 21/3554; G01N 21/314; G01N 2201/062; G01N 1/30; G01N 2001/4027;
(Continued)

(56) References Cited

U.S. PATENT DOCUMENTS

2012/0147375 A1* 6/2012 Nishino ............... G01N 21/314
356/437
2015/0362426 A1* 12/2015 Nishino ............. G01N 21/3554
356/437

FOREIGN PATENT DOCUMENTS

JP H05-141615 A 6/1993
JP H08-312908 A 11/1996
(Continued)

OTHER PUBLICATIONS

Japanese Application No. JP2013-272668, filed Dec. 27, 2014.
(Continued)

*Primary Examiner* — Michael P Stafira
(74) *Attorney, Agent, or Firm* — Amster, Rothstein & Ebenstein, LLP (57) ABSTRACT

A dryness measurement device includes a pipe arranged in a horizontal direction, a light incident portion, and a detecting portion. The light transmitting portion has a solid shape and the light transmitting portion is arranged in a bottom portion of the pipe so that a first portion where a vertical surface crosses a horizontal plane portion of the light transmitting portion is at the same height as a second portion where the vertical surface crosses the lowest part, or so that the first portion is higher than the second portion as well as so that a portion crossing the horizontal plane portion is in the lowest position on a cross line where a cross section of the pipe including a point where light is incident on the horizontal plane portion crosses an inner surface of the pipe and the light transmitting portion.

3 Claims, 10 Drawing Sheets

(51) Int. Cl.
| | |
|---|---|
| *G01N 21/3554* | (2014.01) |
| *G01N 21/85* | (2006.01) |
| *F01K 5/02* | (2006.01) |
| *F01K 13/00* | (2006.01) |
| *G01N 33/18* | (2006.01) |
| *F01K 5/00* | (2006.01) |

(52) U.S. Cl.
CPC ......... *G01N 21/3554* (2013.01); *G01N 21/85* (2013.01); *G01N 33/18* (2013.01); *G01N 2201/12* (2013.01)

(58) Field of Classification Search
CPC ...... G01N 21/359; G01N 25/56; G01N 25/60; G01N 33/367; G01N 7/14; G01N 1/312; G01N 2021/3148; G01N 2021/354; G01N 2021/8521
See application file for complete search history.

(56) References Cited

FOREIGN PATENT DOCUMENTS

| | | |
|---|---|---|
| JP | 2001-27595 A | 1/2001 |
| JP | 2008-281546 A | 11/2008 |
| JP | 2013-092457 A | 5/2013 |
| WO | 2015098279 A | 7/2015 |

OTHER PUBLICATIONS

Giichi Nishino and Yasuhiro Gosho, "Kinsekigaiko o Riyo shita Suijoki no Kawakido Keisoku Gijutsu", Proceedings of the Japanese Symposium on Combustion, Nov. 9, 2011, vol. 49th, pp. 354-355.
Joki no Kawaki Doai Sokutei, Azbil ga Sensor Boiler no Shoene Taisaku ni Michi, Nikkan Kogyo Shinbun, Nov. 21, 2013, p. 8.
International Search Report received for PCT Patent Application No. PCT/JP2014/078830 mailed on Dec. 22, 2014, 4 pages (2 pages of English Translation of International Search Report, 2 pages of International Search Report).

* cited by examiner

DRYNESS MEASUREMENT DEVICE

CROSS-REFERENCE TO RELATED APPLICATIONS

The present application is a National Stage Entry under 35 U.S.C. §371 of International Patent Application No. PCT/JP2014/078830, filed on Oct. 29, 2014, which claims priority to and the benefit of Japanese Patent Application No. 2013-272668, filed on Dec. 27, 2013, the entire contents of each of which are incorporated by reference herein.

TECHNICAL FIELD

The present invention relates to a dryness measurement device.

TECHNICAL BACKGROUND

Water will be wet steam in which a steam gas (a gas phase portion: saturated steam) and water drops (a liquid phase portion: saturated water) are mixed after reaching a boiling point. Here, a weight ratio of the steam gas with respect to wet steam is called "dryness". For example, if there exist the steam gas and the water drops in a ratio of 1:1, the dryness will be 0.5. In a case where there is no water drops and only the steam gas exists, the dryness will be 1.0. It is required to set the dryness of wet steam is close to 1.0 from the viewpoint of using sensible heat and latent heat possessed by wet steam effectively in a heat exchanger and so on, or from the viewpoint of preventing corrosion of turbine blades in a steam turbine. Accordingly, various methods for measuring the dryness have been proposed.

For example, the invention described in Patent Literature 1 relates to a technique of calculating the dryness by calculating a saturated water enthalpy and a saturated steam enthalpy using a saturated steam table based on wet steam flow rates and pressures on the upstream side and the downstream side of a pressure regulating valve by using a fact that the total enthalpy does not change on the upstream side and the downstream side of the pressure regulating valve provided in a pipe.

The invention described in Patent Literature 2 relates to a dryness measurement device including, for measuring the dryness quickly, (a) a light emitting body for irradiating wet steam with light, (b) a photo-receiving element for receiving light transmitted through the wet steam, (c) an environment sensor for measuring a temperature or a pressure of the wet steam, (d) a relationship storing portion for storing the relationship between the intensity of light transmitted through the wet steam and the dryness of the wet steam for each temperature or pressure and (e) a dryness specifying portion for specifying a value of the dryness of wet steam based on the measurement value of the intensity of light in the photo-receiving element, the measurement value of the temperature or the pressure by the environment sensor and the above relationship.

CITATION LIST

Patent Literature

[Patent Literature 1] JP-A-8-312908
[Patent Literature 2] JP-A-2013-092457

SUMMARY OF INVENTION

Problems That the Invention is to Solve

In the inventions described in Patent Literature 1 and Patent Literature 2, the dryness of wet steam is calculated on the theoretical assumption that wet steam flowing in a pipe is distributed with uniform density. However, as a result of keen examination of the relationship between the state of wet steam actually flowing in the pipe and the dryness to be measured by the inventors of the present application, it has been found that there is a problem that the wet steam is not uniformly distributed according to the direction in which the pipe is laid out, and the dryness calculated based on the state of wet steam in a particular portion does not represent a suitable dryness of the entire wet steam.

For example, when an optical path is designed in a vertical direction in the pipe laid out in the horizontal direction, a liquid pool may be formed in a lower part of the pipe in the vertical direction in a related-art sight glass, and thus, it may be difficult to take an accurate measurement of dryness.

In view of the above, an object of the present invention is to provide a dryness measurement device capable of measuring the accurate dryness in the pipe laid out in the horizontal direction.

Means for Solving the Problems

In order to solve the above problem, according to an embodiment of the present invention, there is provided a dryness measurement device according to the present invention including a pipe arranged in a horizontal direction, a light incident portion allowing light to be incident along a vertical surface passing the lowest part of the pipe, a light transmitting portion allowing light transmitted through or reflected on wet steam flowing in the pipe to be transmitted, a detecting portion detecting the intensity of transmitted light and a dryness measurement portion measuring the dryness of the wet steam based on the detected intensity of light, in which the light transmitting portion has a solid shape including a horizontal plane portion and the light transmitting portion is arranged in a bottom portion of the pipe so that a first portion where the vertical surface crosses the horizontal plane portion of the light transmitting portion is in the same height as a second portion where the vertical surface crosses the lowest part, or so that the first portion is higher than the second portion as well as so that a portion crossing the horizontal plane portion is in the lowest position on a cross line where a cross section of the pipe including a point where light is incident on the horizontal plane portion crosses an inner surface of the pipe and the light transmitting portion.

Advantage of the Invention

According to the present invention, as the first portion is at the same height as the second portion or the first portion is higher than the second portion, a liquid pool is not formed. Furthermore, the horizontal plane portion of the light transmitting portion is in the lowest position in the cross section of the pipe, therefore, light passes through a portion having the lowest density in the gas phase portion and the deepest part of the liquid phase portion. Accordingly, the accurate dryness can be measured even in the pipe installed in the horizontal direction.

BRIEF DESCRIPTION OF THE DRAWINGS

FIG. 1A and FIG. 1B show cross-sectional views for explaining a light path of wet steam in a horizontal pipe, in which

FIG. 3A and FIG. 3B show cross sectional views for explaining a light path of wet steam in the horizontal pipe, in which

FIG. 5A and FIG. 5B show cross sectional views for explaining a light path of wet steam in the horizontal pipe, in which

FIG. 6A and FIG. 6B show schematic views of cross lines in which a cross section of the pipe including a point where light incident from a light incident portion is incident on the horizontal plane portion of the light transmitting portion crosses an inner surface of the pipe and the light transmitting portion, in which

FIG. 12A and FIG. 12B show schematic perspective views of a pipe according to a third embodiment of the present invention, in which

FIG. 13A, FIG. 13B, and FIG. 13C show schematic views of the pipe according to the third embodiment of the present invention, in which

MODE FOR CARRYING OUT THE INVENTION

Hereinafter, embodiments of the present invention will be explained with reference to the drawings. Note that the embodiments to be explained below are examples, which do not intend to exclude various alterations and applications of techniques not demonstrated below. That is, the present invention can be achieved by being altered in various manners (by combining respective embodiments) within a scope not departing from the gist thereof. In the following description of the drawings, the same or similar symbols are given to the same or similar components. The drawings are schematic, which do not always correspond to actual sizes, proportions and so on. Portions in which size relationship or the ratio differs from one another may be included in respective drawings.

(Definition)

Primary terms used in the present specification are defined as follows.

"Steam": the steam means water vapor in each of embodiments, but is not limited to the water vapor as long as it is a vapor of a substance to be two phase states including a gas phase portion and a liquid phase portion.

"Dryness": the dryness means a weight ratio between the gas phase portion and the liquid phase portion in the steam. There is a relationship that dryness (%) =100(%)−wetness (%).

"Wet steam": the wet steam means steam with a dryness x of 0 to 100(%).

"Saturated steam": the saturated steam means a gas phase portion of the wet steam. It is also called a "dry saturated steam (saturated dry steam)."

"Saturated water": the saturated water means a liquid phase portion of the wet steam.

"Intensity of light" (Light intensity): the intensity of light means a physical quantity representing the intensity of light (electromagnetic wave), and the appellation and the unit thereof are not limited. The intensity of light corresponds to physical quantities which can be mutually converted though having different units such as the radiant intensity, the luminous intensity, the photon flux intensity and so on.

"Absorbance": the absorbance means a dimensionless quantity indicating to what extent the intensity of light is reduced when the light is transmitted through the wet steam, which is also called an optical density. The absorbance is not limited to the absorption of light but also includes a case where the light intensity is reduced by scattering or reflection.

"Horizontal pipe": the horizontal pipe means a pipe portion arranged so that a projection of the pipe in the axial direction has a horizontal direction component, including a case where the axial direction of the pipe is parallel to the horizontal direction, and a case where the pipe is arranged so that the axial direction makes a fixed angle $\theta(0°<\theta<90°)$ with the horizontal surface. In the "horizontal pipe", the liquid phase portion of the wet steam flowing inside is distributed so as to be biased in one direction on the cross section of the pipe due to gravity.

(Explanation of principles)

Principles of the present invention will be explained with reference to FIG. 1 to FIG. 6B.

Figure 1A:
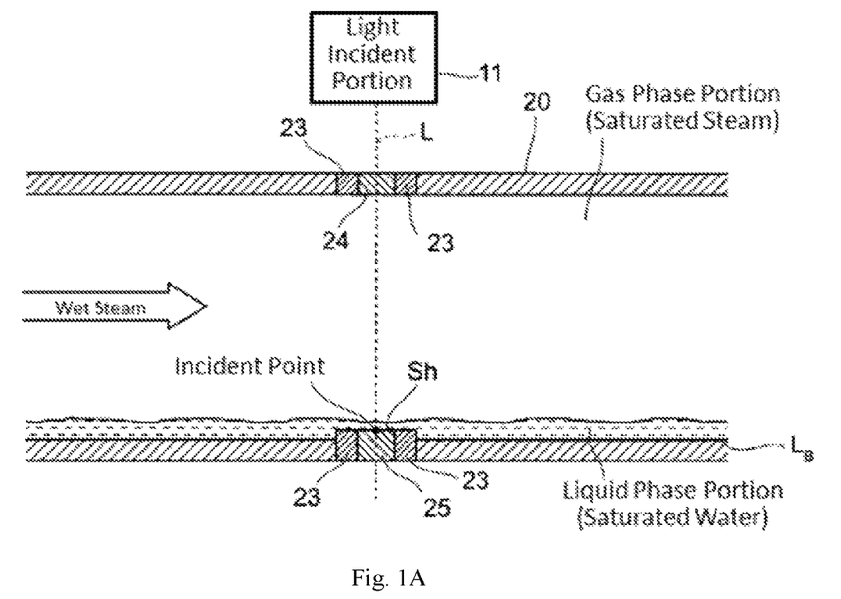
FIG. 1A is a view showing a pipe in which a light transmitting portion is installed and FIG. 1B is an enlarged view of a vicinity of a bottom portion of the pipe in which the light transmitting portion is installed.
Figure 1B:
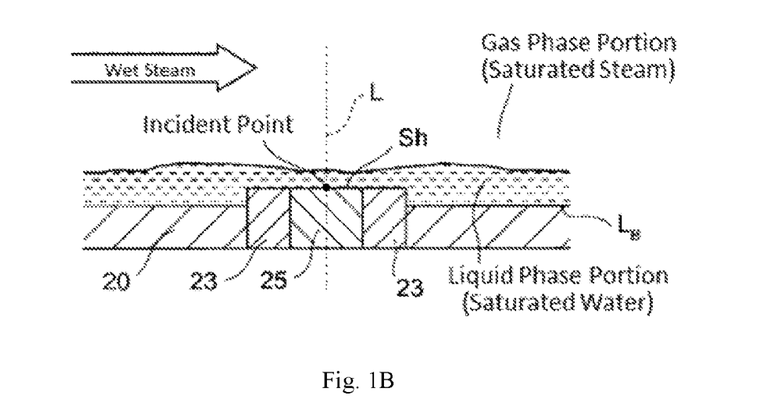
Figure 3A:
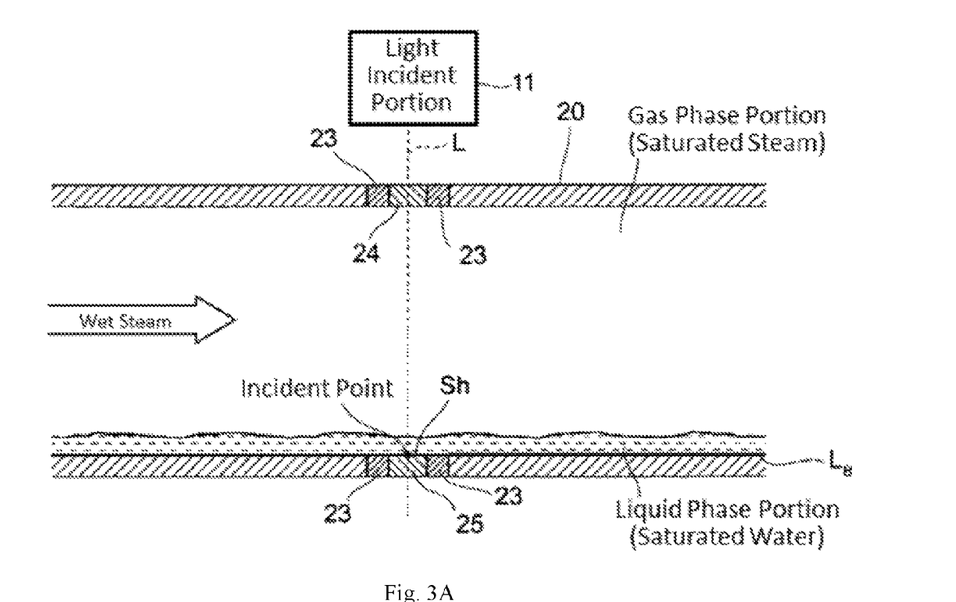
FIG. 3A is a view showing the pipe in which the light transmitting portion is installed and FIG. 3B is an enlarged view of a vicinity of the bottom portion of the pipe in which the light transmitting portion is installed.
Figure 3B:
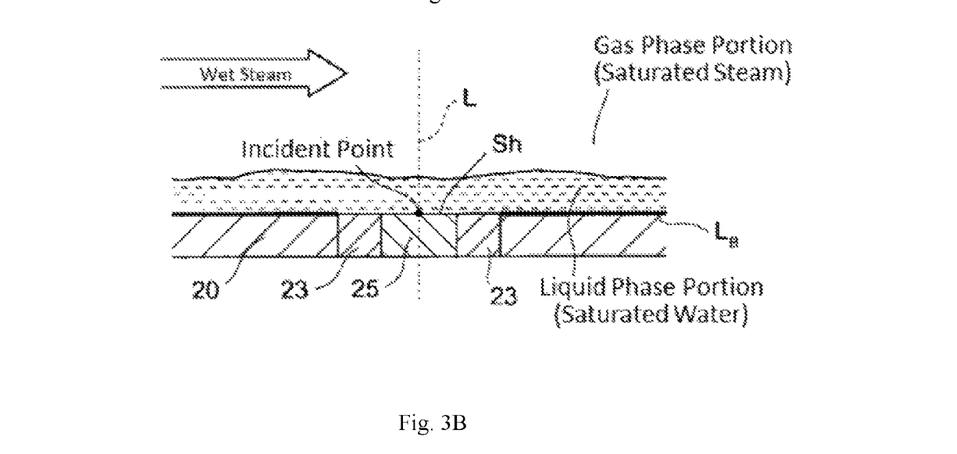
Figure 5A:
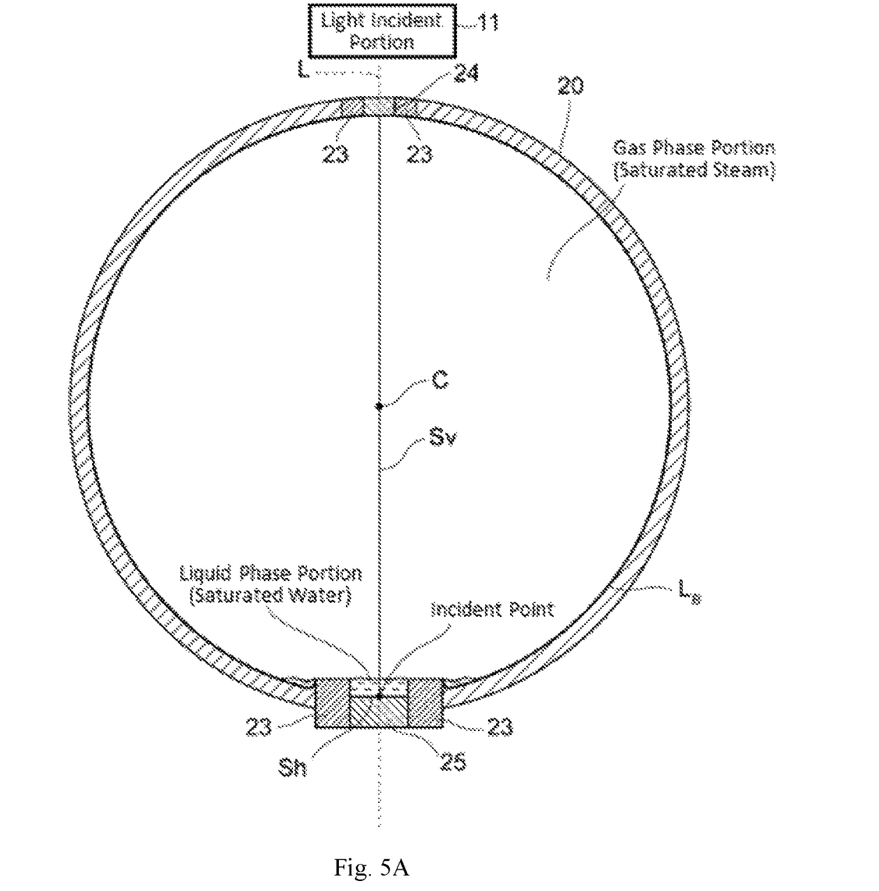
FIG. 5A is a view showing the pipe in which the light transmitting portion is installed and fig. 5B is an enlarged view of a vicinity of the bottom portion of the pipe in which the light transmitting portion is installed.
Figure 5B:
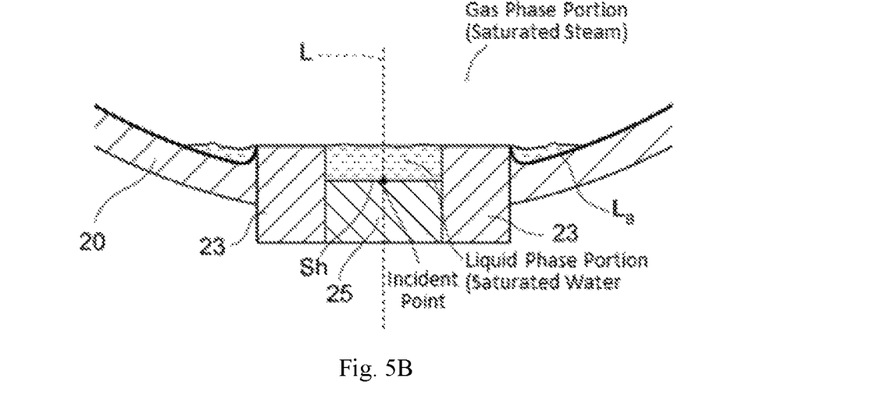

FIG. 1A, FIG. 1B, FIG. 3A, FIG. 3B, FIG. 5A, and FIG. 5B are cross-sectional views for explaining a light path L of wet steam in the horizontal pipe. In particular, FIG. 1A is a view showing a pipe 20 in which a light transmitting portion 25 is arranged, and FIG. 1B is an enlarged view of a vicinity of a bottom portion of the pipe 20 in which the light transmitting portion 25 is arranged. FIG. 3A is a view showing the pipe 20 in which the light transmitting portion 25 is arranged, and FIG. 3B is an enlarged view of a vicinity of the bottom portion of the pipe 20 in which the light transmitting portion 25 is arranged. FIG. 5A is a view showing the pipe 20 in which the light transmitting portion 25 is arranged, and FIG. 5B is an enlarged view of a vicinity of the bottom portion of the pipe 20 in which the light transmitting portion 25 is arranged.

In FIG. 1A and FIG. 1B, the light transmitting portion 25 is arranged in the pipe 20 so that a horizontal plane portion Sh of the light transmitting portion 25 is positioned higher than a lowest part $L_B$ of the pipe 20. In FIG. 3A and FIG. 3B, the light transmitting portion 25 is arranged so that the horizontal plane portion Sh of the light transmitting portion 25 is positioned in the same height as the lowest part $L_B$ of the pipe 20. In FIG. the light transmitting portion 25 is arranged so that the horizontal plane portion Sh of the light transmitting portion 25 is at the lowest position in a cross section of the pipe 20 including a point (incident point) where light is incident on the light transmitting portion 25.

As shown in FIG. 1A, FIG. 1B, FIG. 3A, FIG. 3B, FIG. 5A, and FIG. 5B, when the pipe 20 is the horizontal pipe, the projection of the pipe 20 with respect to the horizontal surface in the axial direction includes the horizontal direction component. The wet steam flowing inside the pipe 20 is distributed so as to be biased on a lower side in the gravity direction in an inner wall of the pipe 20 as a liquid phase portion with a large specific gravity is concentrated by the action of gravity. The surface of the liquid phase portion of the wet steam waves, and the height from the inner wall of the pipe 20 to the surface of the liquid phase portion (the depth of the liquid phase portion) varies. The depth of the liquid phase portion is assumed to be a fixed height obtained by averaging peaks and valleys of waves in the liquid phase portion in the case of the horizontal pipe for making the story simple.

Here, variation in the distribution state of the gas phase portion and the liquid phase portion in the wet steam affects the flow velocity difference or the density difference between the gas phase portion and the liquid phase portion in the wet steam. Variation in the flow velocity difference or the density difference between the gas phase portion and the liquid phase portion in the wet steam directly affects a calculation result of the dryness of wet steam.

As shown in FIG. 1A, FIG. 1B, FIG. 3A, FIG. 3B, FIG. 5A, and FIG. 5B, the distribution of wet steam is biased on the cross section of the pipe 20 in the horizontal pipe. The liquid phase portion with a relatively high specific gravity is distributed so as to be biased on a lower side in the gravity direction, and the gas phase portion with a small specific gravity is distributed so as to be biased on an upper side in the gravity direction. The gas phase portion is also distributed so that the density is increased toward the lower side in the gravity direction and that the density is reduced toward the upper side in the gravity direction. The dryness of wet steam is measured based on the intensity of light transmitted through or reflected on the wet steam. The intensity of light transmitted or reflected is reduced as the density of water molecules is increased. Therefore, the dryness to be measured differs depending on in which direction the light path L incident from a light incident portion 11 is set in the horizontal pipe.

For example, when light for measuring the dryness of wet steam is set so that the light is transmitted only through the gas phase portion, the light is transmitted chiefly through a layer of water molecules with a relatively lower density, therefore, the dryness of wet steam is measured to be higher (closer to "1") than an original correct value. On the other hand, when the light for measuring the dryness of wet steam is set so that the light is transmitted only through the liquid phase portion, the light is transmitted chiefly through a layer of water molecules with a relatively higher density, therefore, the dryness of wet steam is measured to be lower (closer to "0") than an original correct value.

Furthermore, the density of water molecules in the wet steam differs along the vertical direction in the case of the horizontal pipe, therefore, it is necessary to pay attention to the setting of the light path L. In the case where the light path is set in a direction parallel to the horizontal surface even when the path is perpendicular to the axis of the pipe 20, there is a possibility that the dryness to be measured is not a representative value (average value) of the entire wet steam.

Accordingly, when the pipe 20 having a cylindrical shape is the horizontal pipe, the light path L should be set so that light is transmitted through the liquid phase portion of the wet steam flowing along the inner wall of the pipe 20 as shown in FIG. 1A, FIG. 1B, FIG. 3A, FIG. 3B, FIG. 5A, and FIG. 5B. For example, in the case where the pipe 20 has an axisymmetric cylindrical shape as shown in FIG. 5A and FIG. 5B, the light path L is set along a plane including an axial center C of the pipe 20, namely, a plane parallel to a direction of the axial center C. When the light path L is set so that the light constantly passes through the liquid phase portion in the case where the liquid phase portion is generated in wet steam, light for measuring the wet steam passes through a portion having the highest density in the wet steam, therefore, the dryness of wet steam to be measured is considered to be equivalent to the correct dryness of the wet steam. That is, the light path L should be set so that light is incident along a vertical surface Sv passing the lowest part $L_B$ of the pipe 20 as shown in FIG. 5B. It is not always necessary to set the light path L so that light is incident vertically as long as the light is incident along the vertical surface Sv. That is because the light path L passing the deepest part of the liquid phase portion is set if only the light is incident along the vertical surface Sv passing the lowest part $L_B$, therefore, the correct dryness is reflected.

In other words, it is preferable that the light path L for measuring wet steam is set so that light is transmitted through the part having the lowest density in the gas phase portion of wet steam and the deepest part in the liquid phase portion of wet steam in the horizontal pipe.

In the case where the cross-sectional shape of the pipe 20 is not a perfect circle, that is, in the case where the pipe 20 does not have the axisymmetric cylindrical shape, the plane including the axial center C of the pipe 20 does not always pass the portion having the most lowest density and the portion having the most highest density. The deepest part of the liquid phase portion is a portion where the saturated water in a liquid phase state tends to be stored easily as well as a portion where the density is the highest. Accordingly, even when the pipe 20 have a shape which is not symmetrical to the axial center C, it can be considered that the dryness to be measured in the light path represents the correct dryness of wet steam as long as light transmits through the portion having the lowest density in the gas phase portion and the deepest part in the liquid phase portion of wet steam of the pipe 20.

However, in the case there the light path L along the vertical surface Sv passing the lowest part $L_B$ of the horizontal pipe is designed as described above, a liquid pool is formed in a lower part of the pipe 20 in the vertical direction when the horizontal plane portion in an observation window installed in the pipe 20 is lower than the lowest part of the pipe as in a related-art sight glass of the horizontal pipe. Although the liquid phase portion of wet steam normally flows in the same direction as a flowing direction of the wet steam, the liquid phase portion of wet steam is retained in the portion where the liquid pool exists when the liquid pool is formed in the lower part of the pipe 20 in the vertical direction. Accordingly, if the liquid pool is formed once, the liquid phase portion remains in the part of the light transmitting portion 25 even when the dryness changes and the flow rate of the liquid phase portion changes, incident light is transmitted through dry steam including the remaining gas phase portion, errors are naturally increased in the dryness which is measured in accordance with the relative area ratio between the liquid phase portion and the gas phase portion, as a result, there is a possibility that the accurate dryness of wet steam is not obtained. Therefore, in order to achieve one of the objects of the present invention, it is necessary to satisfy another condition in addition to the above condition. Accordingly, another condition will be explained below.

Figure 2:
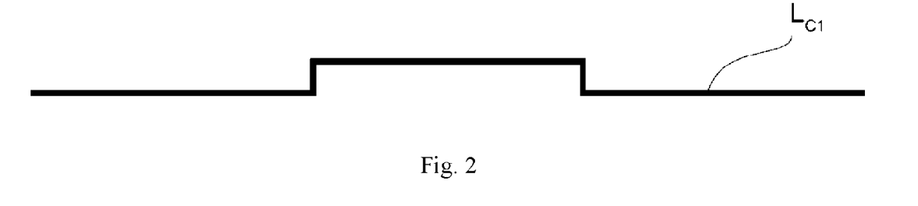
FIG. 2 is a schematic view of a cross line crossing the lowest part of the pipe and the light transmitting portion based on FIG. 1A and FIG. 1B.
Figure 4:
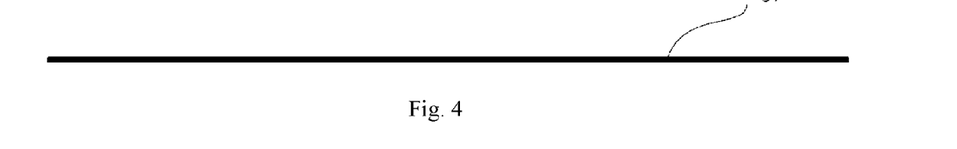
FIG. 4 is a schematic view of a cross line crossing the lowest part of the pipe and the light transmitting portion based on FIG. 3A and FIG. 3B.
Figure 6A:
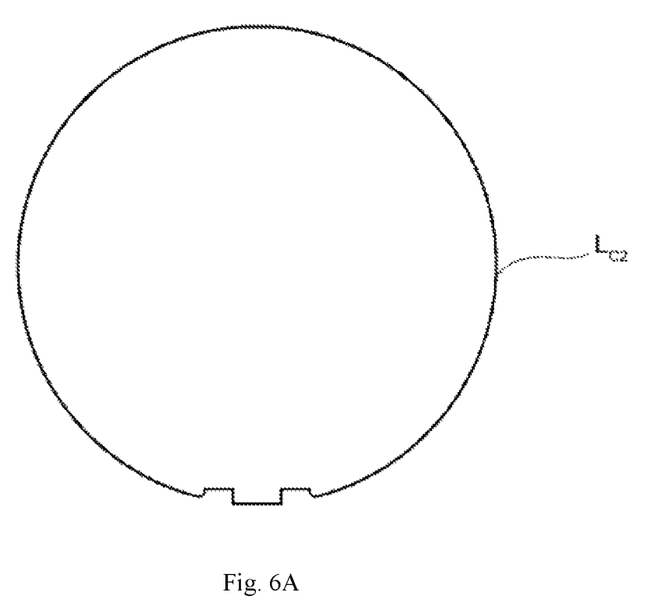
FIG. 6A is a schematic view of a cross line based on FIG. 5A and FIG. 5B
Figure 6B:
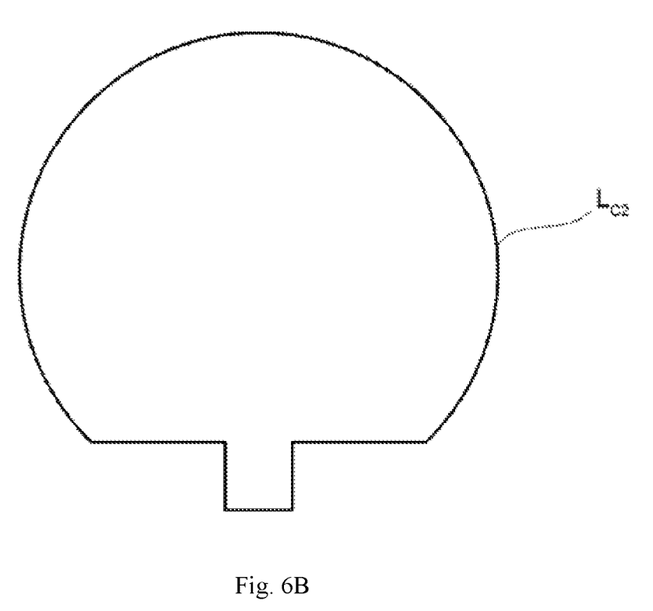
FIG. 6B is a schematic view showing an example of another cross line.

FIG. 2 is a conceptual view obtained by extracting only a cross line $L_{C1}$ where the vertical surface Sv crosses the lowest part and the light transmitting portion 25 of the pipe 20 in FIG. 1A and FIG. 1B. FIG. 4 is a conceptual view obtained by extracting only a cross line $L_{C1}$ where the vertical surface Sv crosses the lowest part and the light transmitting portion 25 of the pipe 20 in FIG. 3A and FIG. 3B. FIG. 6A and FIG. 6B show schematic views of a cross line where a cross section of the pipe 20 including a point where the light incident from the light incident portion 11 is incident on the horizontal plane portion Sh of the light transmitting portion 25 crosses an inner surface of the pipe 20 and the light transmitting portion 25, and particularly, FIG. 6A is a schematic view of a cross line where the cross section of the pipe 20 crosses the inner surface of the pipe 20 and the light transmitting portion 25, which corresponds to FIG. 5A and FIG. 5B.

As shown in FIG. 4, the light transmitting portion 25 is preferably arranged so that a first portion where the vertical surface Sv crosses the horizontal plane portion Sh of the light transmitting portion 25 is in the same height as a second portion where the vertical surface Sv crosses the lowest part $L_B$, in other words, the light transmitting portion 25 is preferably arranged so that a portion crossing the horizontal plane portion Sh of the light transmitting portion 25 is in the same height as the lowest part $L_B$ of the pipe 20 on the cross line $L_{C1}$ (first cross line) where the vertical surface Sv crosses the lowest part $L_B$ and the horizontal plane portion Sh of the light transmitting portion 25. According to the arrangement, in the cross line $L_{C1}$ where the vertical surface Sv crosses the lowest part $L_B$ and the horizontal plane portion Sh of light transmitting portion 25, the height in the vertical direction does not change at any place as shown in FIG. 4, therefore, the liquid pool of the liquid phase portion is not formed on the light transmitting portion 25 even when the liquid phase portion of dry steam is increased or reduced.

Furthermore, in the case where the lowest part $L_B$ of the pipe 20 and the horizontal plane portion Sh of the light transmitting portion 25 are made to have different heights as shown in FIG. 2, the light transmitting portion 25 is preferably set so that the first portion where the vertical surface Sv crosses the horizontal plane portion Sh of the light transmitting portion 25 is higher than the second portion where the vertical surface Sv crosses the lowest part $L_B$, in other words, the light transmitting portion 25 is preferably arranged so that the portion crossing the horizontal plane portion Sh of the light transmitting portion 25 is the highest on the cross line $L_{C1}$ (first cross line). According to the arrangement, in the cross line $L_{C1}$ where the vertical surface Sv crosses the lowest part $L_B$ and the horizontal plane portion Sh of light transmitting portion 25, the height of the horizontal plane portion Sh of light transmitting portion 25 at least corresponds to the highest portion of the liquid phase portion, therefore, the liquid pool of the liquid phase portion is not formed on the light transmitting portion 25 even when the liquid phase portion is increased or reduced in dry steam.

Furthermore, in the cross section of the pipe 20, it is preferable that the light transmitting portion 25 is arranged in a bottom portion of the pipe 20 so that the portion crossing the horizontal plane portion Sh of the light transmitting portion 25 is in the lowest position on a cross line $L_{C2}$ (second cross line) (cross line shown in FIG. 6A and FIG. 6B) in which the cross section of the pipe 20 including the point (incident point) where light incident from the light incident portion 11 is incident on the horizontal plane portion Sh of the light transmitting portion 25 crosses the inner surface of the pipe 20 and the light transmitting portion 25 (the light transmitting portion 25 and a support portion 23) as shown in FIG. 6A and FIG. 6B. According to the arrangement, the horizontal plane portion Sh of the light transmitting portion 25 is provided in the lowest part on the cross section of the pipe 20 as shown in the second cross line $L_{C2}$ of FIG. 6A, therefore, the deepest part of the liquid phase portion of dry steam is formed on an upper surface of the horizontal plane portion Sh. Accordingly, light incident from the light incident portion 11 passes through the portion having the lowest density in the gas phase portion of the pipe 20, therefore, the accurate dryness can be measured.

The arrangement of the light transmitting part 25 with respect to the pipe 20 is not limited to the states shown in FIG. 2, FIG. 4 and FIG. 6A as long as the above condition is satisfied. For example, FIG. 6B is a schematic view showing a modification example of the second cross line $L_{C2}$ of FIG. 6A. Although sizes of the light transmitting portion 25 and the support portion 23 installed in the pipe 20 are small and the light transmitting portion 25 and the support portion 23 are formed to be attachable/detachable with respect to the pipe 20 in FIG. 6A, sizes of the light transmitting portion 25 and the support portion 23 are larger than those of FIG. 6A and are formed to be previously incorporated as part of the pipe 20 (so as not to be attachable/detachable). Such structure is also included.

[First Embodiment]

In view of the above principles, respective embodiments of the present invention will be explained. A dryness measurement device according to a first embodiment of the present invention will be explained with reference to FIG. 7.

(Structure and Operation)

Figure 7:
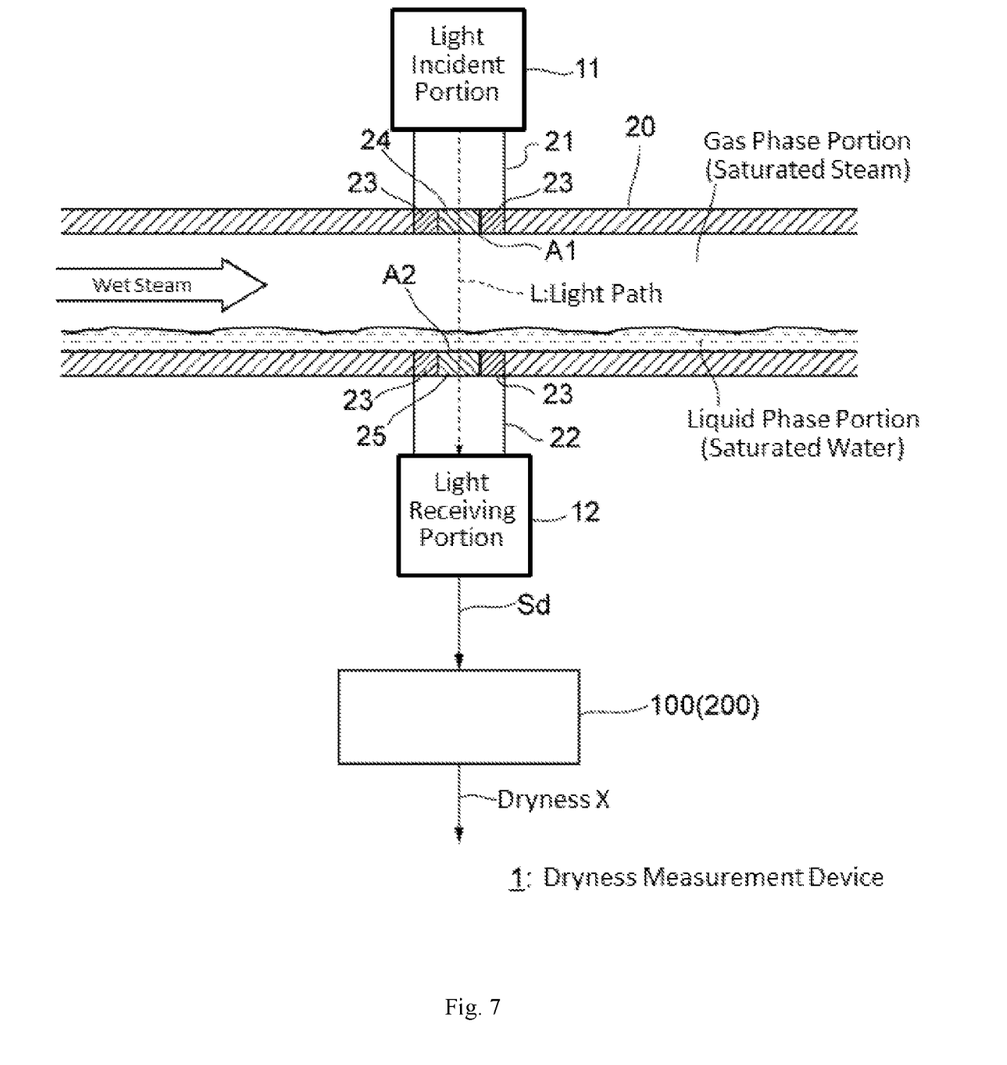
FIG. 7 is a schematic view of a dryness measurement device according to a first embodiment of the present invention.

FIG. 7 is a schematic view of a dryness measurement device 1 according to the first embodiment of the present invention. As shown in FIG. 7, the pipe 20 is a fluid flow passage through which wet steam to be measured flows, and the light path L for allowing light to pass is provided inside the pipe 20. An incident opening A1 and an emission opening A2 are provided in the inner wall of the pipe 20. The incident opening A1 and the emission opening A2 are provided so as to face each other with respect to the axial center C of the pipe 20. An incident side cylinder 21 is connected to the incident opening A1, and an emission side cylinder 22 is provided in the emission opening A2. According to the structure, the light path L for measuring the dryness of wet steam is provided so as to penetrate the pipe 20.

Next, a structure of the dryness measurement device 1 according to the first embodiment will be explained. As shown in FIG. 7, the dryness measurement device 1 according to the first embodiment is illustratively configured to include the light incident portion 11, a light receiving portion 12, the pipe 20, the incident side cylinder 21, the emission side cylinder 22, the support portion 23, an incident window 24, the light transmitting portion 25 and a computer device 100 (dryness measurement portion 200). It is not necessary that the dryness measurement device 1 has all the components, and the device can be configured to include part of them. For example, the dryness measurement device 1 may include at least the light incident portion 11, the light receiving portion 12 and the computer device 100 (dryness measurement portion 200). The dryness measurement device 1 may have a structure not having the support portion 23. Furthermore, the support portion 23 may be included in the pipe 20 though the support portion 23 is different from the pipe 20 in the explanation of the embodiment of the present invention.

The light incident portion 11 allows light to be incident on the pipe 20 in which wet steam to me measured flows along the light path L which has been previously set.

The light incident portion 11 may be a self-light emitting means for emitting light by itself and may be a light guide means for guiding light emitted from a light emitting means at a separated place. As self-light emitting means, for example, a light emitting diode, a super luminescent diode, a semiconductor laser, a laser oscillator, a fluorescent discharge tube, a low-pressure mercury lamp, a Xenon lamp, a halogen lamp, a metal-halide lamp, an ultraviolet light source, an infrared light source, a light bulb and so on can be cited as examples, however, the means are not limited to the above as long as they can emit light having a stable wavelength and intensity. As light guide means, a plastic optical fiber made of polymethylmethacrylate resin (PMMA: Poly (methyl methacrylate), a glass optical fiber made of quartz glass and so on can be cited as examples, however, the means are not limited to the above as long as they have a function of propagating light emitted by the self-light emitting means which are cited above.

The light receiving portion 12 is a light detection means for detecting an intensity of light To transmitted through or reflected on wet steam. Specifically, the light receiving portion 12 receives light transmitted through the wet steam along the light path L and emitted from the emission opening A2 through the light transmitting portion 25 installed in the pipe 20 with the support portion 23 which supports the light transmitting portion 25 and further through the emission side cylinder 22, and outputs a light intensity signal Sd corresponding to the intensity of light.

As the light receiving portion 12, for example, photoelectric conversion elements such as a photodiode and a phototransistor can be used, however, the light receiving portion 12 is not limited to them as long as the device can output the light intensity signal Sd corresponding to the intensity of light transmitted through or reflected on the wet steam.

The light transmitting portion 25 has a solid shape including the horizontal plane portion Sh. As the light transmitting portion 25, for example, glass having heat resistance, pressure resistance or corrosion resistance can be cited, however, the light transmitting portion 25 is not limited to the above as long as the portion can transmit light. The light transmitting portion 25 may have various types of solid shapes corresponding to the shape of an insertion port 35 in the support portion 23, for example, may have solid shapes such as a convex solid shape, a frustum shape and a plate-like solid shape, which will be described later.

The computer device 100 is a calculating means functioning as the dryness measurement portion 200 according to the present invention, which specifies the dryness of wet steam based on the detected intensity of light. The computer device 100 includes, as an example, a CPU (Central Processing Unit), a RAM (Random Access Memory), a ROM (Read Only Memory) and an interface (I/F) circuit, though not shown. For example, an external storage device (not shown) is connected to the computer device 100. The external storage device stores, for example, a software program for allowing the computer device 100 to execute the method of measuring the dryness according to the present invention. When the computer device 100 reads the software program relating to the dryness measurement method according to the present invention stored in the external storage device or the like and executes the program, the dryness measurement portion 200 is functionally realized.

The dryness measurement portion 200 is configured to calculate a dryness x of wet steam based on the intensity of light detected by the light receiving portion 12, an area of the gas phase portion and an area of the liquid phase portion of wet steam corresponding to the intensity of light, a velocity difference between the gas phase portion and the liquid phase portion of wet steam and a density difference between the gas phase portion and the liquid phase portion of wet steam.

It is not necessary that the dryness measurement portion 200 calculates the dryness x of wet steam based on all items described above, which are the intensity of light detected by the light receiving portion 12, the area of the gas phase portion and the area of the liquid phase portion of wet steam corresponding to the intensity of light, the velocity difference between the gas phase portion and the liquid phase portion of wet steam and the density difference between the gas phase portion and the liquid phase portion of wet steam, and the dryness measurement portion 200 may calculate the dryness x by using part of the above information. Furthermore, the dryness measurement portion 200 may calculate absorbance of wet steam with reference to the light intensity signal Sd based on the detected intensity of light and may calculate the dryness x of wet steam based on the absorbance.

The dryness measurement portion 200 may be configured to calculate also the amount of saturated steam and the amount of saturated water in the process of measuring the dryness x based on the intensity of light received by the light receiving portion 12 or the absorbance A obtained from the intensity of incident light and the intensity of light received by the light receiving portion 12.

Figure 8:
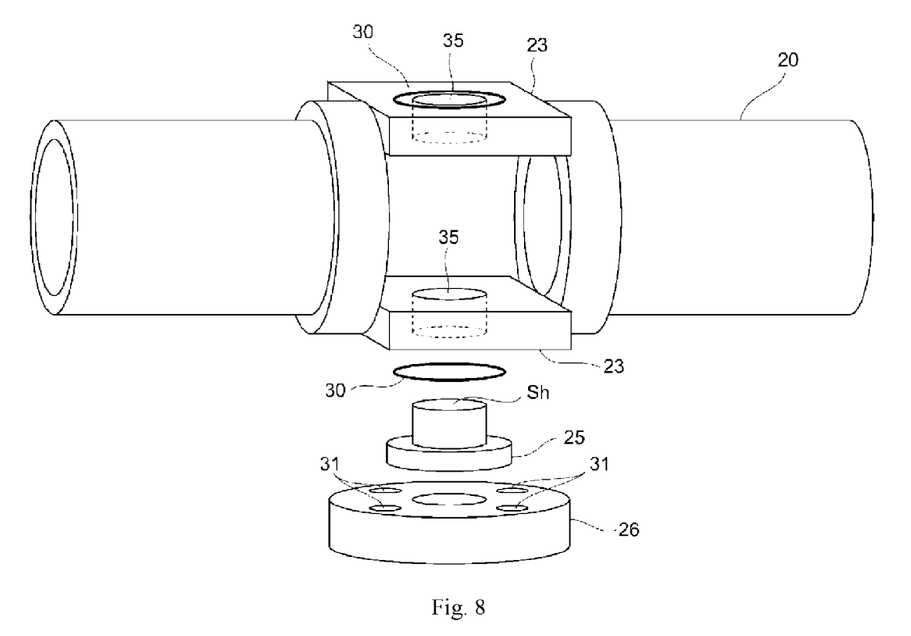
FIG. 8 is an exploded perspective view of a pipe according to the first embodiment of the present invention.
Figure 9:
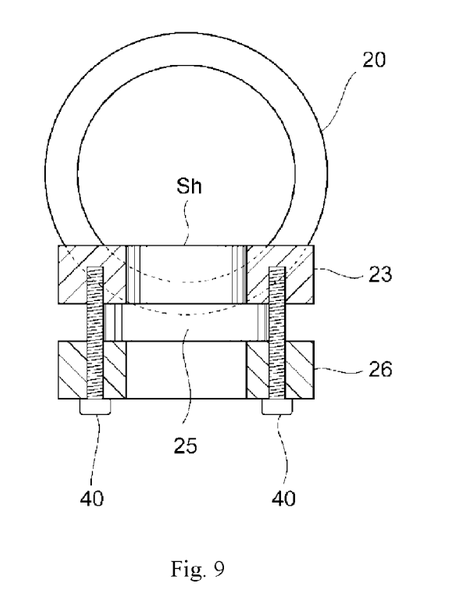
FIG. 9 is a schematic cross-sectional view of the pipe according to the first embodiment of the present invention.

Next, the dryness measuring device 1 according to the first embodiment of the present invention is explained with reference to FIG. 8 and FIG. 9. FIG. 8 and FIG. 9 are schematic views of the pipe according to the first embodiment of the present invention. In particular, FIG. 8 is a front view of the pipe 20 and FIG. 9 is a cross-sectional view of the pipe 20.

As shown in FIG. 8 and FIG. 9, the dryness measurement device 1 according to the first embodiment illustratively includes the pipe 20, the support portions 23, the light transmitting portion 25, a pedestal 26, gaskets 30, holes 31, the insertion ports 35 and bolts 40. Holes (not shown) formed in the support portion 23 and the holes 31 formed in the pedestal 26 have a threaded structure. The light transmitting portion 25 has a shape of the convex solid shape.

The dryness measuring device 1 according to the first embodiment of the present invention is provided with supported portions 23 on the upper side and the lower side respectively. The support portions 23 have the insertion ports 35 having a cylindrical shape, and the light transmitting portion 25 having the horizontal plane portion Sh on the top is inserted into the insertion port 35 from the lower side of the pipe 20. Here, the light transmitting portion 25 is arranged in a bottom portion of the pipe 20 so that the first portion where the vertical surface Sv passing the lowest part $L_B$ of the pipe 20 crosses the horizontal plane portion Sh of the light transmitting portion 25 is in the same height as the second portion where the vertical surface Sv crosses the lowest part $L_B$ of the pipe 20, or so that the first portion is higher than the second portion as well as so that the portion crossing the horizontal plane portion Sh of the light transmitting portion 25 is in the lowest position on a cross line where the cross section of the pipe 20 including the point where light is incident on the horizontal plane portion Sh of the light transmitting portion 25 crosses the inner surface of the pipe 20 and the light transmitting portion 25.

Also as shown in FIG. 8 and FIG. 9, the gasket 30 is arranged between the support portion 23 and the light transmitting portion 25 for preventing leakage of wet steam. Furthermore, the light transmitting portion 25 is pressed from the lower side of the light transmitting portion 25 by using the pedestal 26 for increasing the sealing property in the pipe 20. At that time, the bolts 40 are screwed and fastened to the threaded structure formed in the holes 31 provided in the pedestal 26 and the holes (not shown) provided in the support portion 23.

According to the structure, the dryness measurement device 1 according to the first embodiment can measure the accurate dryness by the pipe laid out in the horizontal direction, and particularly, the dryness measurement device 1 according to the first embodiment can further increase the sealing property inside the pipe 20, the mechanical strength and stability by screwing and fastening the bolts 40 to the threaded structure formed in the holes 31 provided in the pedestal 26 and the holes (not shown) provided in the support portion 23.

In FIG. 8 and FIG. 9, the support portion 23 has the insertion port 35 having the cylindrical shape, however, the shape is not limited as long as it is the shape into which the light transmitting portion 25 can be inserted. Although the light transmitting portion 25 has the convex solid shape, it may be a frustum shape having the horizontal plane portion Sh on the top and so on. Shapes corresponding to the shape of the insertion port 35 provided in the support portion 23 can be adopted. Furthermore, the horizontal plane portion Sh of the light transmitting portion 25 may be polygonal shapes other than the circular shape.

[Second Embodiment]

Figure 10:
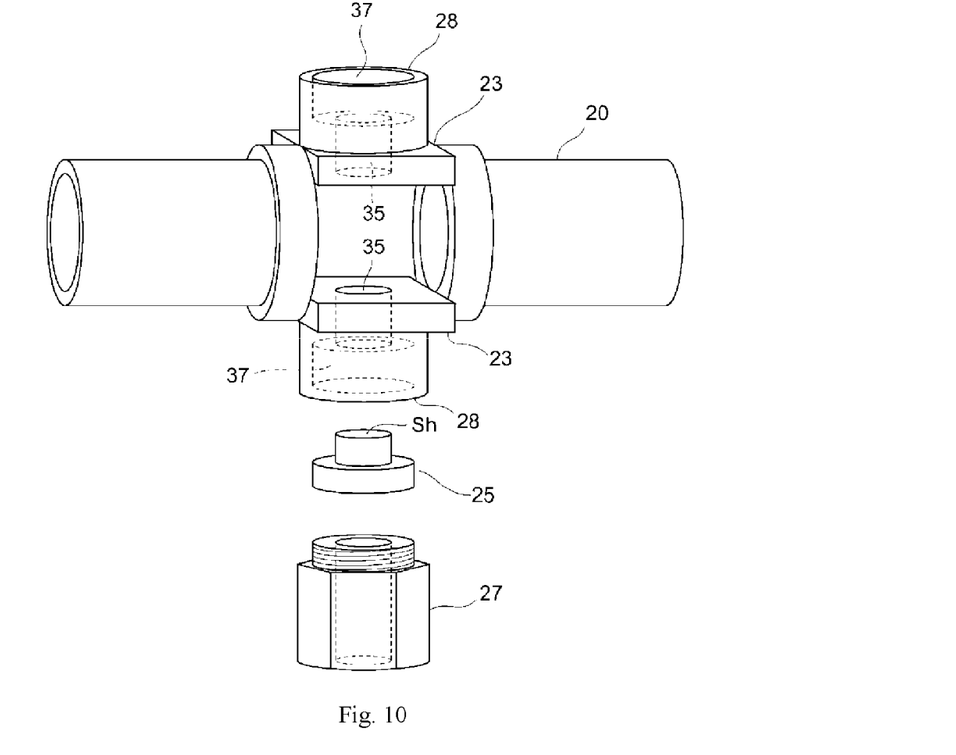
FIG. 10 is an exploded perspective view of a pipe according to a second embodiment of the present invention.
Figure 11:
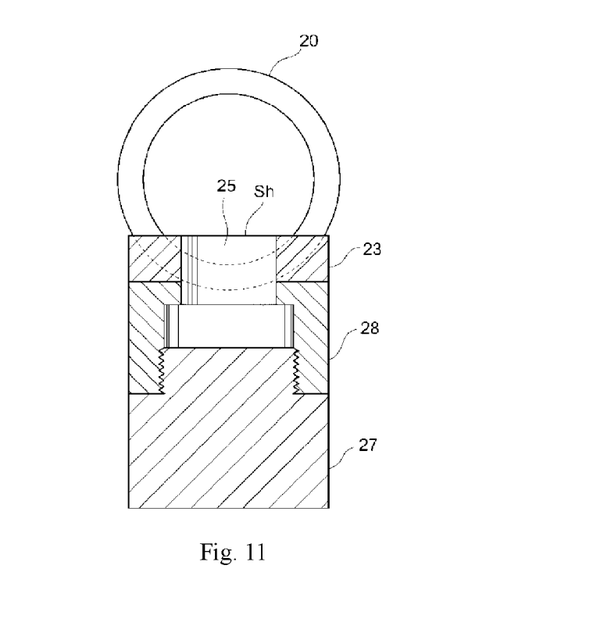
FIG. 11 is a schematic cross-sectional view of the pipe according to the second embodiment of the present invention.

Next, the dryness measurement device 1 according to a second embodiment of the present invention will be explained with FIG. 10 and FIG. 11. FIG. 10 and FIG. 11 are schematic views of the pipe according to the second embodiment of the present invention. In particular, FIG. 10 is a front view of the pipe 20 and FIG. 11 is a cross-sectional view of the pipe 20.

As shown in FIG. 10 and FIG. 11, the dryness measurement device 1 according to the second embodiment illustratively includes the pipe 20, the support portions 23, the light transmitting portion 25, a screw 27, joints 28, the insertion ports 35 and insertion ports 37. The pipe 20 of the dryness measurement device 1 according to the second embodiment has a joint structure. The light transmitting portion 25 has the shape of the convex solid shape.

The dryness measurement device 1 according to the second embodiment is provided with supported portions 23 on the upper side and the lower side respectively. The support portions 23 have the insertion ports 35 having a cylindrical shape. The light transmitting portion 25 having the convex solid shape including the horizontal plane surface Sh on the top is inserted into the support portion 23, and the joint 28 having the insertion port 37 to which the screw 27 for pushing or supporting the light transmitting portion 25 from the lower side of the light transmitting portion 25 is installed.

According to the structure, the dryness measurement device 1 according to the second embodiment can measure the accurate dryness by the pipe laid out in the horizontal direction, and particularly, the dryness measurement device 1 (particularly the pipe 20) according to the second embodiment can be constructed easily and can increase the sealing property inside the pipe 20, the mechanical strength and stability by making the pipe 20 as the joint structure.

Although the pipe 20, the support portions 23 and the joints 28 are explained as separate components in the embodiment, these may be integrally formed or part of them may be integrally formed. The light transmitting portion 25 is arranged in the bottom portion of the pipe 20 so that the first portion where the vertical surface Sv passing the lowest part $L_B$ of the pipe 20 crosses the horizontal plane portion Sh of the light transmitting portion 25 is in the same height as the second portion where the vertical surface Sv crosses the lowest part $L_B$ of the pipe 20, or so that the first portion is higher than the second portion as well as so that the portion crossing the horizontal plane portion Sh of the light transmitting portion 25 is in the lowest position on the cross line where the cross section of the pipe 20 including the point where light is incident on the horizontal plane portion Sh of the light transmitting portion 25 crosses the inner surface of the pipe 20 and the light transmitting portion 25.

In FIG. 10 and FIG. 11, the support portion 23 has the insertion port 35 having the cylindrical shape, however, the shape is not limited as long as it is the shape into which the light transmitting portion 25 can be inserted. Although the light transmitting portion 25 has the convex solid shape, it may be the frustum shape having the horizontal plane portion Sh on the top and so on. Shapes corresponding to the shape of the insertion port 35 provided in the support portion 23 can be adopted. Furthermore, the horizontal plane portion Sh of the light transmitting portion 25 may be polygonal shapes other than the circular shape.

[Third Embodiment]

Figure 12A:
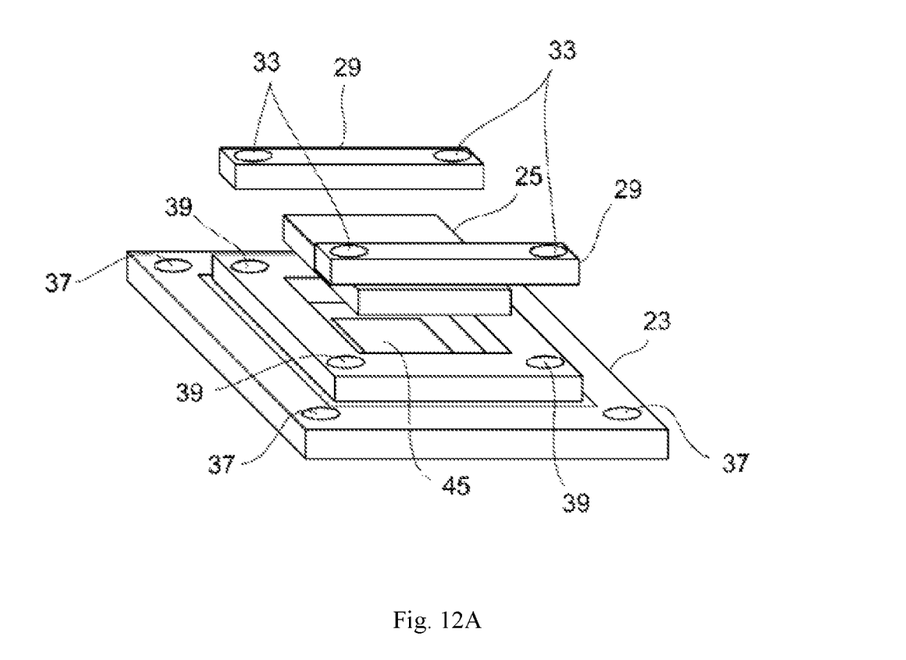
FIG. 12A is a view showing a state before the light transmitting portion is installed in a support portion provided in the pipe and FIG. 12B is a view showing a state after the light transmitting portion is installed in the support portion provided in the pipe.
Figure 12B:
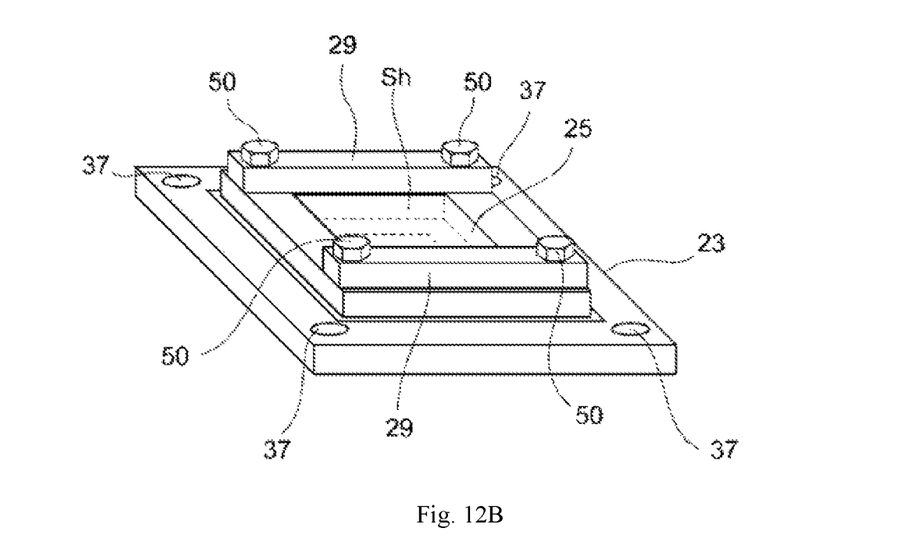
Figure 13A:
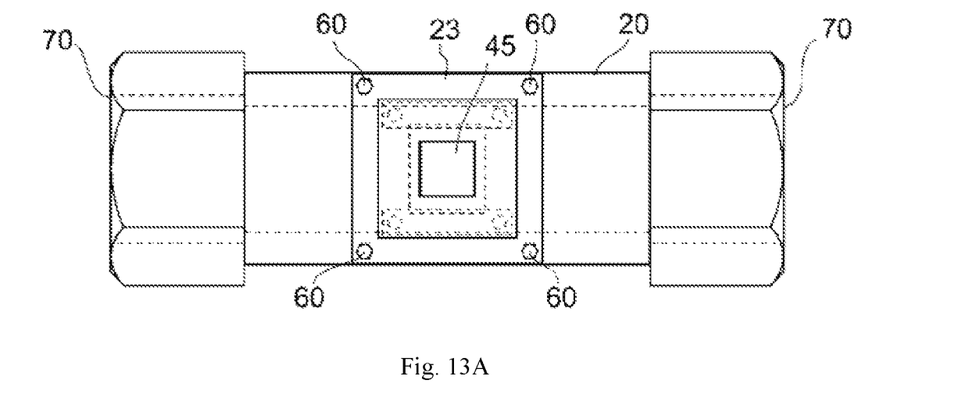
FIG. 13A is a plan view.
Figure 13B:
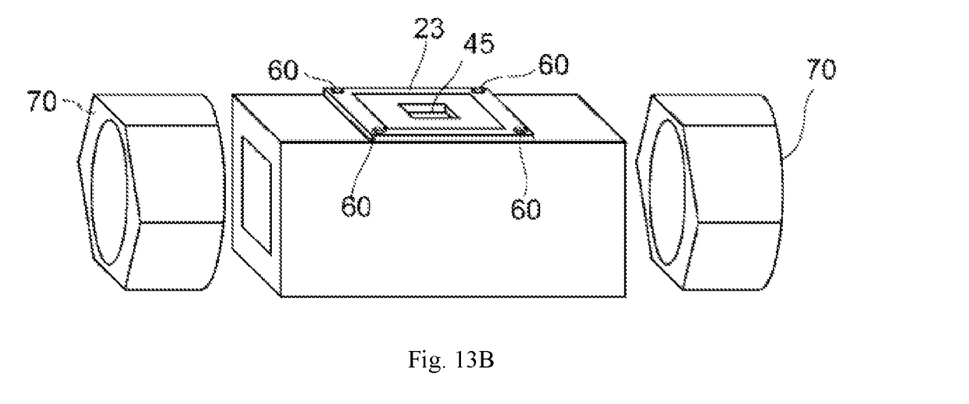
FIG. 13B is an exploded perspective view and FIG. 13C is a front view.
Figure 13C:
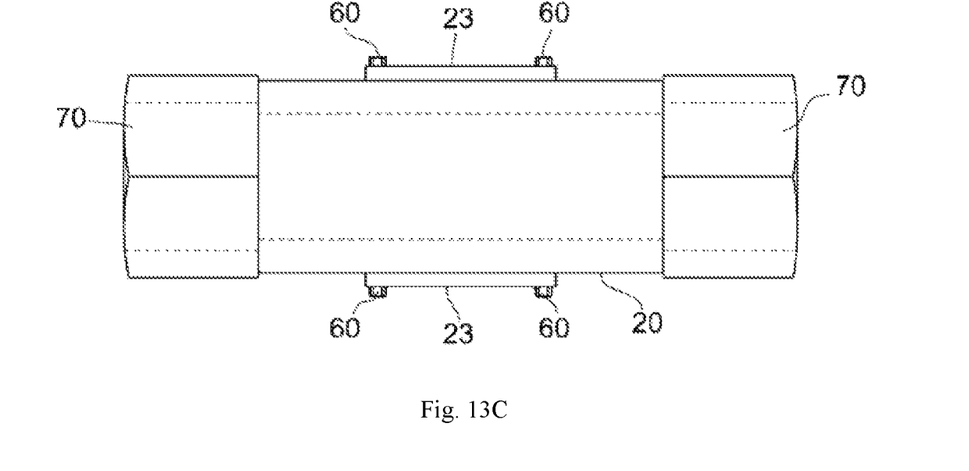
Figure 14:
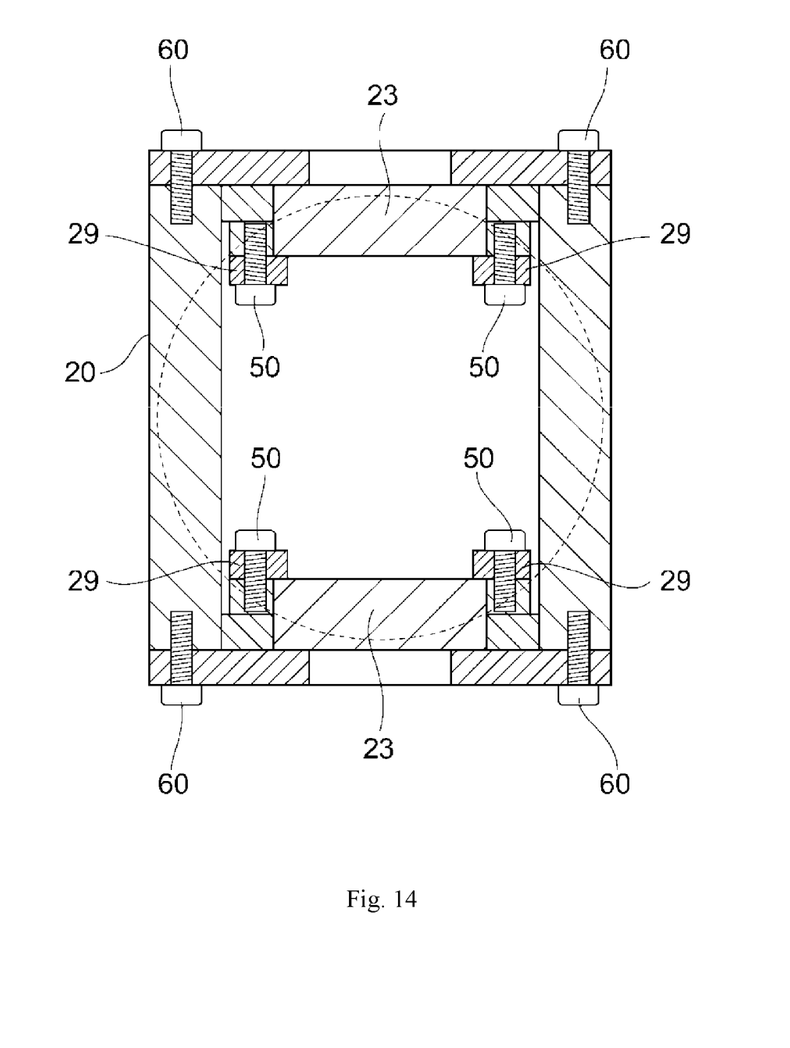
FIG. 14 is a schematic cross-sectional view of the pipe according to the third embodiment of the present invention.

Next, the dryness measurement device 1 according to a third embodiment of the present invention will be explained with FIG. 12A, FIG. 12B, FIG. 13A FIG. 13B and FIG. 14. In particular, FIG. 12A is a view showing a state before the light transmitting portion is installed in the support portion provided in the pipe and FIG. 12B is a view showing a state after the light transmitting portion is installed in the support portion provided in the pipe. FIG. 13A, FIG. 13B, and FIG. 13C are a plan view, an exploded view and a front view of the pipe 20, and FIG. 14 is a cross-sectional view of a cross section including the pipe 20, the support portion 23 and the light transmitting portion 25.

As shown in FIG. 12A, FIG. 12B, FIG. 13A, FIG. 13B, and FIG. 14, the dryness measurement device 1 according to the third embodiment of the present invention illustratively includes the pipe 20, the support portions 23, the light transmitting portion 25, pressing members 29, holes 33, 37 and 39, an insertion port 45, screws 50, 60 and joints 70. The light transmitting portion 25 has a shape of the plate-like solid shape.

The dryness measurement device 1 according to the third embodiment is provided with supported portions 23 on the upper side and the lower side respectively. In particular, as shown in FIGS. 12(*a*) and (*b*), the support portion 23 includes the insertion port 45 having a plate-like shape, and the light transmitting portion 25 having the plate-like solid shape including the horizontal plane portion Sh is inserted into the support portion 23.

As the light transmitting portion 25 is pressed from the upper side of the light transmitting 25 by the pressing members 29 for pressing the light transmitting portion 25 which have the holes 33, the light transmitting portion 25 is fixed in the insertion port 45 of the support portion 23. At that time, the screws 50 are screwed and fastened to the threaded structure formed in the holes 39 provided in the support portion 23 through the holes 33 provided in the pressing members 29.

Furthermore, the screws 60 are screwed and fastened to the threaded structure formed in holes (not shown) provided in the pipe 20 through the holes 37 provided in the support portion 23. Accordingly, the support portion 23 is installed in the pipe 20.

According to the structure, the dryness measurement device 1 according to the third embodiment can measure the accurate dryness by the pipe laid out in the horizontal direction, and particularly, even when the light transmitting portion 25 is thin in thickness, the light transmitting portion 25 can be suitably installed in the pipe 20.

As shown in FIG. 13B, the joints 70 may be configured to connect to the pipe 20 so as to be removed from the pipe 20. Although the support portion 23 has the plate-like shaped insertion portion 45 in FIG. 12A and FIG. 12B, however, the shape is not limited as long as it is a shape into which the light transmitting portion 25 can be inserted. The light emitting portion 25 has the plate-like solid shape, however, it may also be formed in a cylindrical shape having the horizontal plane portion Sh at the top, and shapes corresponding to the shape of the insertion port 45 provided in the support portion 23 can be adopted. Furthermore, the horizontal plane portion Sh of the light transmitting portion 25 may be polygonal shapes other than the square shape.

Although the pipe 20, the support portions 23 and the joints 70 are explained as separate components in the embodiment, these may be integrally formed or part of them may be integrally formed. The light transmitting portion 25 is arranged in the bottom portion of the pipe 20 so that the first portion where the vertical surface Sv passing the lowest part $L_B$ of the pipe 20 crosses the horizontal plane portion Sh of the light transmitting portion 25 is in the same height as the second portion where the vertical surface Sv crosses the lowest part $L_B$ of the pipe 20, or so that the first portion is higher than the second portion as well as so that the portion crossing the horizontal plane portion Sh of the light transmitting portion 25 is in the lowest position on the cross line where the cross section of the pipe 20 including the point where light is incident on the horizontal plane portion Sh of the light transmitting portion 25 crosses the inner surface of the pipe 20 and the light transmitting portion 25.

In FIG. 12 and FIG. 13, the support portion 23 has the insertion port 45 having a plate-like shape, however, the shape is not limited as long as it is the shape into which the light transmitting portion 25 can be inserted. Although the light transmitting portion 25 has the plate-like solid shape, it may be the frustum shape having the horizontal plane portion on the top and so on. Shapes corresponding to the shape of the insertion port 45 provided in the support portion 23 can be adopted.

Respective components included in the above respective embodiments can be combined in a technically possible range, and these combinations are included in claims of the present invention as long as they include characteristics of the present invention.

INDUSTRIAL APPLICABILITY

The dryness measurement device 1 according to the present invention can be applied to a steam pipe using a steam boiler and so on, manufacturing process equipment performing heating, drying and chemical reactions by using the steam, and particularly applied to pipes or equipment requiring the horizontal pipe.

DESCRIPTION OF REFERENCE NUMERALS AND SIGNS 1 dryness measurement device
11 light incident portion
12 light receiving portion
20 pipe
21 incident side cylinder
22 emission side cylinder
23 support portion
24 incident window
25 light transmitting portion
100 computer device
200 dryness measurement portion
A1 incident opening
A2 emission opening
L light path
Sd light intensity signal
Sh horizontal plane portion of light transmitting portion
x dryness.

The invention claimed is:
1. A dryness measurement device comprising:
a pipe arranged in a horizontal direction;
a light incident portion allowing light to be incident along a vertical surface passing a lowest part of the pipe;
a light transmitting portion allowing light transmitted through or reflected on wet steam flowing in the pipe to be transmitted;
a detecting portion detecting an intensity of transmitted light; and
a dryness measurement portion measuring a dryness of the wet steam based on the detected intensity of light,
wherein the light transmitting portion has a solid shape including a horizontal plane portion and the light transmitting portion is arranged in a bottom portion of the pipe so that a first portion where the vertical surface crosses the horizontal plane portion of the light transmitting portion is higher than a second portion where the vertical surface crosses the lowest part, as well as so that a portion crossing the horizontal plane portion is in a lowest position on a cross line where a cross section of the pipe including a point where light is incident on the horizontal plane portion crosses an inner surface of the pipe and the light transmitting portion.
2. The dryness measurement device according to claim 1, further comprising:
a support portion supporting the light transmitting portion.
3. The dryness measurement device according to claim 1, wherein the light transmitting portion has one or more solid shapes selected from a group including a convex solid shape, a frustum shape and a plate-like solid shape, and wherein a top portion of the one or more solid shapes forms the horizontal plane portion.

* * * * *